US009414767B2

(12) United States Patent
Speier

(10) Patent No.: US 9,414,767 B2
(45) Date of Patent: Aug. 16, 2016

(54) METHOD AND EKG TRIGGER DEVICE FOR CORRECTING AN EKG SIGNAL IN MAGNETIC RESONANCE IMAGE ACQUISITION

(71) Applicant: Siemens Aktiengesellschaft, Munich (DE)

(72) Inventor: Peter Speier, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 113 days.

(21) Appl. No.: 14/260,632

(22) Filed: Apr. 24, 2014

(65) Prior Publication Data
US 2014/0323850 A1 Oct. 30, 2014

(30) Foreign Application Priority Data
Apr. 24, 2013 (DE) .......................... 10 2013 207 458

(51) Int. Cl.
*A61B 5/055* (2006.01)
*A61B 5/0456* (2006.01)
*A61B 5/00* (2006.01)

(52) U.S. Cl.
CPC .............. *A61B 5/055* (2013.01); *A61B 5/0456* (2013.01); *A61B 5/7203* (2013.01); *A61B 5/7285* (2013.01); *A61B 5/7289* (2013.01)

(58) Field of Classification Search
USPC ....................................................... 600/413
See application file for complete search history.

(56) References Cited

U.S. PATENT DOCUMENTS

| 8,150,492 | B2* | 4/2012 | Demharter | A61B 5/0402 600/411 |
| 8,509,883 | B2* | 8/2013 | Rossler | A61B 5/0456 600/509 |
| 2003/0095263 | A1* | 5/2003 | Varshneya | A61B 5/113 356/477 |
| 2007/0066886 | A1* | 3/2007 | Kuhara | G01R 33/5673 600/413 |

(Continued)

OTHER PUBLICATIONS

Philip J. Allen, Giovanni Polizzi, Karsten Krakow, David R. Fiish, and Louis Lemieux, "Identification of EEG Events in the MR Scanner: The Problem of Pulse Artifact and a Method for Its Subtraction", Neuroimage 8, 229-239 (1998).*

(Continued)

*Primary Examiner* — Tse Chen
*Assistant Examiner* — Joanne Hoffman
(74) *Attorney, Agent, or Firm* — Schiff Hardin LLP

(57) ABSTRACT

In a method to correct an EKG signal, the EKG signal is acquired, and used for R-spike triggering, during a magnetic resonance (MR) image acquisition sequence that produces interference signals in the EKG signal generated by gradient jumps, wherein the gradient jumps repeat at a fixed time interval, and wherein the duration of a cardiac cycle measured via the EKG signal is at least five times the time interval. During at least a first cardiac cycle, immediately after detection of the R-spike in the EKG signal no detection of the R-spike for triggering takes place for a dead time that is shorter than the duration of the cardiac cycle and during which the MR sequence is already running, and the EKG signal is acquired in that dead time as a reference signal. The reference signal is analyzed to extract interference signals that respectively repeat after the time interval, which are used to determine a correction signal having a duration equal to the time interval. During the further execution of the MR sequence, the correction signal, which is synchronously repeated in the time interval, at least outside of the dead time, is used to correct the measured EKG signal.

14 Claims, 2 Drawing Sheets

(56) References Cited

U.S. PATENT DOCUMENTS

| | | | |
|---|---|---|---|
| 2008/0154121 A1* | 6/2008 | Kouwenhoven | G01R 33/5673 600/413 |
| 2009/0088654 A1* | 4/2009 | Demharter | A61B 5/0428 600/509 |
| 2010/0277173 A1* | 11/2010 | Landschuetz | A61B 5/055 324/309 |
| 2011/0181285 A1* | 7/2011 | Greiser | A61B 5/055 324/309 |

OTHER PUBLICATIONS

Dima Abi-Abdallah, Eric Chauvet, Latifa Bouchet-Fakri, Alain Bataillard, André Briguet and Odette Fokapu, "Reference signal extraction from corrupted ECG using wavelet decomposition for MRI sequence triggering: application to small animals", BioMedical Engineering OnLine, 5:11, 1-12 (2006).*

* cited by examiner

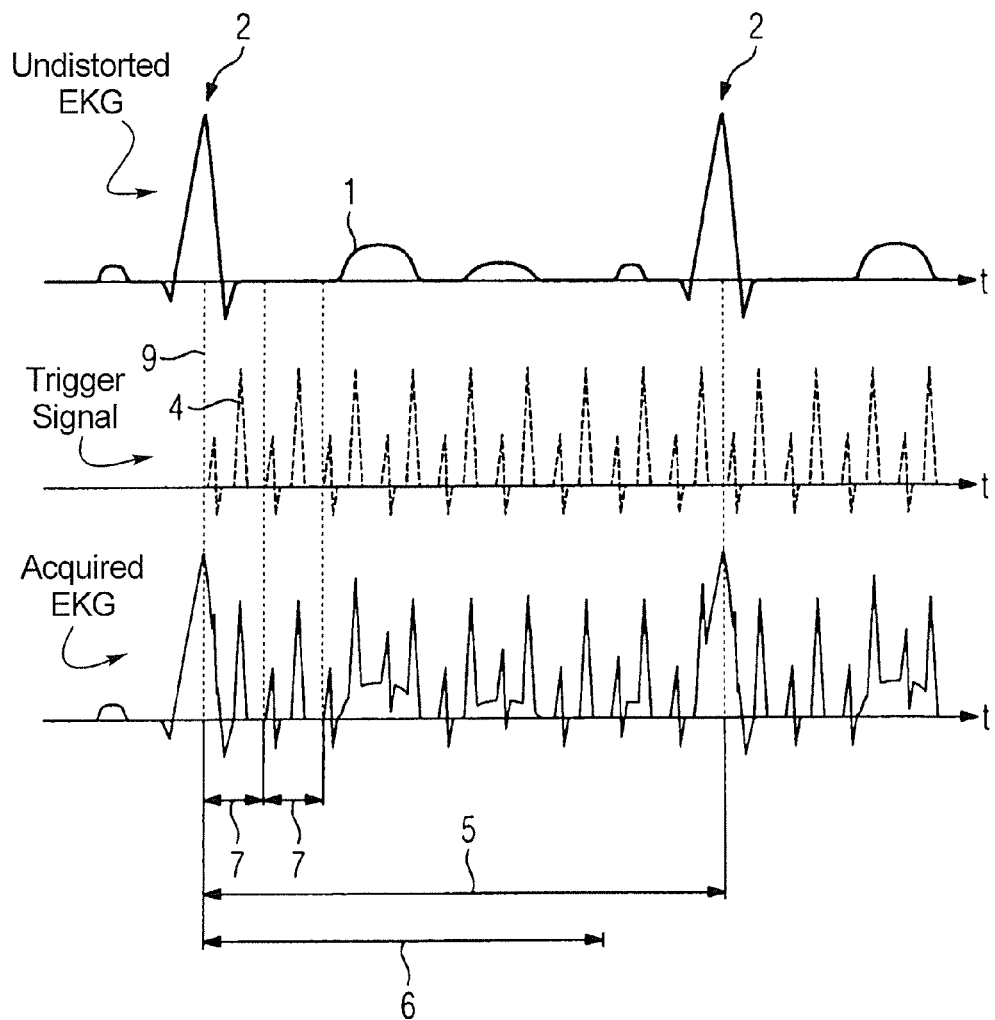

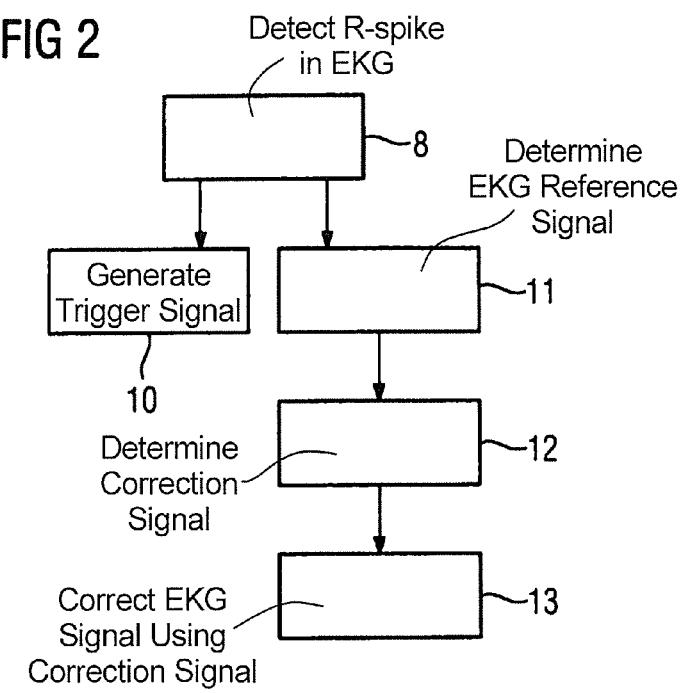
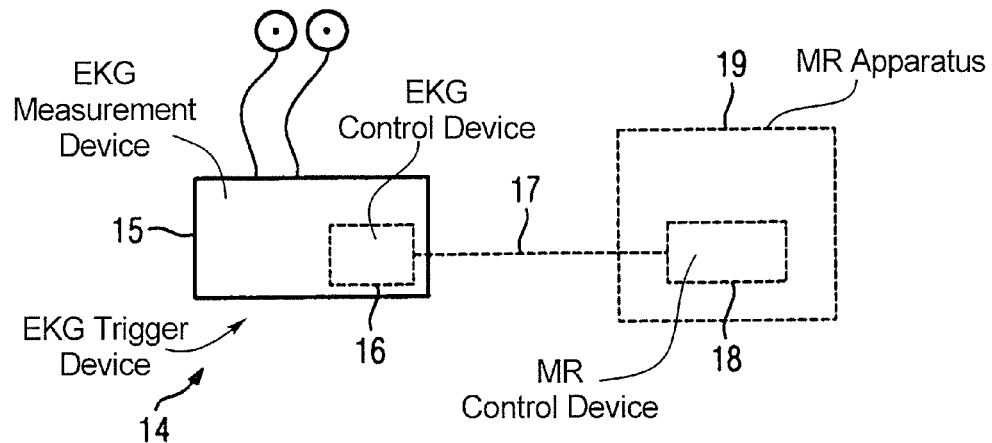

METHOD AND EKG TRIGGER DEVICE FOR CORRECTING AN EKG SIGNAL IN MAGNETIC RESONANCE IMAGE ACQUISITION

BACKGROUND OF THE INVENTION

1. Field of the Invention

The present invention concerns: a method for correcting an EKG signal, acquired during an image acquisition with a magnetic resonance (MR) device according to a magnetic resonance sequence, for interference signals generated by magnetic gradient field jumps that occur during the magnetic resonance sequence, as well as an EKG trigger device for a magnetic resonance measurement.

2. Description of the Prior Art

Magnetic resonance imaging is an established imaging modality that is used especially often in medicine. In many applications, it is the case that the image acquisition must be synchronized with physiological processes, either in order to achieve an optimal image quality or to allow an evaluation of the acquired magnetic resonance data. With regard to cardiac imaging, it is necessary to synchronize the image acquisition with the beating heart. For this purpose, it is typical to measure the EKG signal of the patient via an EKG measurement device and to detect the R-spike in real time. When the R-spike of the EKG signal has been detected, a trigger signal is sent to the running magnetic resonance sequence. For use within the framework of the evaluation of the acquired magnetic resonance data, this trigger signal is stored with the magnetic resonance data but can also be used in order to start defined imaging processes or portions of magnetic resonance sequences (the readout, for example).

However, within the scope of magnetic resonance measurement problems occur in the measurement of the EKG signal because two sources exist that generate unwanted interference signals. One type of such signals is oscillating signals that originate from electrically conductive blood flow (magneto-hydrodynamic effect). Additionally, spike-like signals occur due to currents that are induced due to variations of the gradient fields in the electrical circuits that are created by the patient and the EKG wires. Such chronological variations of gradient fields (gradient ramps, for example) that are defined by the magnetic resonance sequence are generally designated as gradient jumps (discontinuities) in the following. In some sequences, interference signals due to gradient jumps can be strong enough to overlap the actual EKG signal, such that the detection algorithm fails.

In order to enable a robust triggering, the R-spike must also be reliably detectable in the presence of these artifacts. A few solutions have been proposed for this purpose.

A first approach proposes to use alternative trigger mechanisms in addition to EKG triggering, for example optical pulse triggering or acoustic triggering which, however, disadvantageously require additional hardware. In addition, further disadvantages exist in comparison to EKG measurement, in particular a method-related, non-negligible delay from the R-spike peak to the generated trigger signal, which makes this method unsuitable for high-quality cine-imaging in which the triggering should occur before the beginning of the heart contraction.

The measurement of an EKG signal consequently remains as the standard, clinically proven triggering method. A multitude of developments and solution approaches exist that should make the EKG triggering more robust, in particular highly complex signal filtering and the use of multiple EKG wires in order to measure a vector EKG. In spite of all this research work, methods are known in which the success rate of the method is approximately 95%, for example, which means that—according to this example—a triggering error can currently occur in 5% of patients, which can lead to approximately one failure per day in a cardiac center, for example. A further improvement of a triggering with an EKG signal is consequently desirable in magnetic resonance imaging.

Further improvements in EKG triggering with regard to their robustness can be expected only if application-specific optimizations of the detection algorithms for the R-spike are considered. Clinical standard protocols can be divided into two groups:

1. Static imaging, wherein the spin preparation and the acquisition of a fraction of the cardiac cycle are limited. Also included in this imaging group is perfusion imaging (also called dynamic imaging), in which the measurement of multiple spin-prepared slices is completed in one heartbeat, after which a repetition takes place (for example over 10 seconds at cardiac cycles) in order to monitor a dynamic process, for example the first pass of a contrast agent bolus ("first pass measurement").

2. Cine-imaging, wherein an acquisition takes place over the entire cardiac cycle in order to generate a four-dimensional image data set (thus a film) of the heart movement. More complex methods are also known, for example the technique known as "tagging", in which at the beginning the image acquisition is preceded by a spin preparation that follows the trigger signal.

Static imaging methods can use a trigger signal that is determined with a considerable delay in comparison to the peak of the R-spike. In order to improve the imaging for this family of applications, it has been proposed to detect the entire R-spike instead of only its rising edge. This method increases the available information about the shape of the signal, such that the R-spike can be clearly differentiated from interference signals in the EKG signal. In this method, however, a considerable delay also occurs from the peak of the R-spike to the point in time of the trigger signal, such that it is unsuitable for cine-imaging.

An additional known way to improve the robustness of a triggering is to monitor the gradient activity of the running magnetic resonance sequence in order to identify and eliminate gradient spikes in the EKG signal. For this procedure it is necessary to measure the gradient activity and to make it accessible to the analysis algorithm for the EKG signal. For example, such a measurement can be achieved by dedicated pick-up coils or be transferred immediately from the gradient control unit to the EKG trigger device. This external gradient activity information must be converted into artifacts in the EKG signal in order to enable an elimination of the interference signals. This multi-parameter conversion requires a pre-calibration, for example by monitoring reference gradient activity. A high cost, and high demands on the electronics implementing the method, consequently are associated with this method.

SUMMARY OF THE INVENTION

An object of the invention is to provide a method, which is in particular suitable for cine-imaging, for elimination of interference signals due to gradient jumps in the EKG signal, which requires no up-to-date external gradient activity information, no additional hardware, and no additional communication, and also does not require a pre-calibration.

This object is achieved in a method of the aforementioned type wherein an R-spike to be used as a trigger is detected from the EKG signal, the magnetic resonance sequence has at least one gradient jump that causes an identical interference signal, this gradient jump being repeated at a fixed time interval (in particular a repetition time), and the duration of a cardiac cycle measured with the EKG signal corresponds to at least five times (in particular ten times) the time interval. In accordance with the invention, during at least a first cardiac cycle, immediately after detection of the R-spike in the EKG signal no detection of the R-spike takes place for a dead time that is shorter than the duration of the cardiac cycle and during which the magnetic resonance sequence is already running, and the EKG signal is acquired as a reference signal. By analysis of the reference signal, interference signals that respectively repeat after the time interval are extracted and used to determine a correction signal whose duration corresponds to the time interval. During the further workflow of the magnetic resonance sequence, the correction signal, which is synchronously repeated in the time interval, at least outside of the dead time, is used to correct the measured EKG signal, in particular is subtracted from the measured EKG signal.

As explained, the expression "gradient jump" as used herein means temporal variations of gradient fields that occur within the scope of the magnetic resonance sequence, which variations are generated in particular by ramps in the gradient curve in which gradients are activated, for example, as is fundamentally known. Interference signals can occur that should be corrected by the present method in order to improve the robustness of the detection of an R-spike that serves as a trigger. This means that, given detection of the R-spike, a trigger signal is generated that is stored with the magnetic resonance data for a later evaluation, or that can affect the operation of the magnetic resonance device, for example by initiating a readout process.

The present invention is based on the insight that some requirements that are most often present, particularly in cine-imaging, provide a possibility to correct the EKG signal for interference signals caused by the gradient jumps that is simple to realize and does not require up-to-date, external information. The first key insight of the present invention is consequently to use the fact that the gradient activity of many magnetic resonance sequences (in particular the cine-sequences) repeats in a time interval (the repetition time TR), wherein multiple such repetitions occur within a heartbeat; more than ten repetitions (time intervals) are guaranteed in typical cine-sequences. In most cases, the magnetic resonance sequence is entirely repetitive; in other cases, this means that the generated interferences are at least approximately comparable. The duration of a repetition—thus the time interval—is thus already known in the preparation of the protocol, but can also be derived from the correction signal by analysis in many cases.

The second fundamental insight of the present invention is that, after an R-spike, a guaranteed time period exists in which no R-spikes are expected, such that this time period can be used to learn the pattern of the gradient activity. At this point, it is noted that a guaranteed time that is free of R-spikes many not always exist given severe arrhythmias of the heart, but known magnetic resonance sequences are not suitable anyway to deal with such circumstances, such that the discussion of the present invention applies to relatively regular cardiac cycles. The invention uses a dead time after detection of the R-spike, which can also be designated as a "trigger lock time". Such a "trigger lock time" is known and designates the time period in which no R-spike detection takes place via the detection algorithm. For hardware that is currently in use, this dead time has a minimum value of 300 ms, which means that at least 6 repetitions fall within this guaranteed minimum dead time given a typical repetition time (thus a time interval) that is less than 50 ms. However, this is sufficient in order to allow an analysis of the recurring interference signal pattern in the reference signal acquired during the dead time. This means that the dead time—in which no detection of the R-spike takes place anyway—is used to acquire a reference signal from which a correction signal can be extracted, which correction signal includes the periodically recurring interference signals due to the gradient jumps.

However, if this correction signal is first known, it can be subtracted from the EKG signal in a time-synchronized manner (because it is known that the interference signals due to the gradient jumps respectively repeat after a time interval), at least when the R-spike detection is actively operated. However, the interference signals in the EKG signal that are generated by the gradient jumps therefore fall away, and a markedly more robust triggering is provided. The method thereby proceeds without up-to-date external information about the gradients because parameters (in particular the repetition time TR) that are always already present in all cases well before the beginning of the image acquisition are used by the analysis algorithm for the reference signal. Additional hardware, or fast communication with which the EKG signal to be acquired is processed, are not required. Also, a pre-calibration is not necessary since the reference signal is acquired at a time at which no R-spike occurs anyway, consequently no separation of the interference signals from the R-spike is required.

Other correction variants are also conceivable in addition to a subtraction, for example the addition of the correction signal to an expected comparison signal used for comparison, or the use of a filter adapted to the correction signal, is which filter the measured EKG signal is processed.

Overall, the method according to the invention combines the knowledge of the time that is free of R-spikes; the fact that the magnetic resonance sequence is repetitive; and the knowledge that multiple repetitions occur within the time free of R-spikes, in order to achieve a simple and advantageous procedure to obtain a marked increase of the robustness of an EKG triggering for the magnetic resonance sequences that satisfy the cited basic conditions.

In a further embodiment of the present invention, the magnetic resonance sequence is started at the latest during the dead time after detection of the R-spike of the first cardiac cycle. It can consequently be appropriate to ensure the correct detection of the R-spike before the first dead time (in which the reference signal is then acquired), by beginning the magnetic resonance sequence only after the R-spike. For example, the magnetic resonance sequence is started by a trigger signal determined from this first dead time. This further increases the reliability of the method.

It is also advantageous for the dead time to be determined from a current heart rate, in particular in the range of one third to two thirds of the duration of a cardiac cycle. This means that the shortest possible dead time does not necessarily need to be used (as was described above); rather, it is advantageous to define this depending on the current heart rate (which is determined anyway by the EKG measurement device), such that there is greater certainty that no R-spike occurs in the dead time. For example, it is possible to determine the dead time as two thirds of the duration of a cardiac cycle. It is precisely in cine-imaging that it is reasonable to set the dead time to quite a high value, because the film quality is extremely poor if a trigger signal is emitted far too early. It is even conceivable to also select the dead time to be greater than two thirds of the cardiac cycle, in particular when a regular heartbeat can be assumed. The dead time can consequently also be at least two thirds of the expected interval between two R-spikes.

As already noted, it is conceivable in principle to conclude the time interval (in particular the repetition time) from the analysis of the reference signal itself by detecting recurring patterns, which is particularly the case when the interference signals differ sufficiently due to different gradient jumps within the magnetic resonance sequence. However, it is preferable for the time interval (in particular the repetition time) to be determined before the first cardiac cycle and to be considered in the analysis of the reference signal. For example, the repetition time TR is a parameter that is already known well before the actual magnetic resonance measurement, namely in the preparation of the magnetic resonance protocol. For example, the repetition time can be stored in a control device of the magnetic resonance device with the magnetic resonance protocol and/or be included in the DICOM parameter "TR". Well before the beginning of the image acquisition with the magnetic resonance sequence, the repetition time is transferred to the computer (for example a control device of the EKG trigger device) implementing the method according to the invention so that it is available to the algorithms. Such a communication channel is already known because the magnetic resonance sequence in the prior art parameterizes the trigger algorithm anyway, for example supplies a trigger source, a triggering method, and the like.

For analysis of the reference signal it is advantageous to define successive sub-time windows, which correspond in duration to the time interval, in the reference signal, wherein the partial signals in the sub-time windows are averaged to determine the correction signal. In this way, a simple learning algorithm can be applied in that partial signals corresponding to the time interval within the reference signal (or reference signals, if multiple reference signals are acquired) are considered with equal weight, for which sub-time windows are defined whose length is the time interval. By such an averaging, non-periodic signals (for example those that originate from the magneto-hydrodynamic effect) are suppressed relative to the periodic pattern.

For magnetic resonance sequences with a preparation segment in which the periodic repetition of the gradient jumps is not yet present, no acquisition and/or analysis of the reference signal takes place in accordance with the invention at their start for the duration of the preparation segment, and/or the first cardiac cycle is selected depending on the duration of the preparation segment. It is precisely in the field of cine-magnetic resonance that sequences are used in which the repetitive pattern does not start immediately after the trigger signal, but rather a spin preparation module (thus a spin preparation segment) is activated in advance of the data acquisition, for example in order to achieve an inversion for the T1 estimation or to define a tagging module within the scope of a load analysis. In order to also cover such cases, an offset time describing the duration of the preparation segment can also be transferred (for example together with the repetition time) to the EKG trigger device or the corresponding algorithms well before the beginning of the magnetic resonance measurement, such that the duration of the preparation segment is known and can be taken into account accordingly in the evaluation of the reference signal.

In a further embodiment of the method, an additional reference signal is acquired in at least one additional cardiac cycle after the first cardiac cycle, and is evaluated for adaptation of the correction signal. Because the dead time is present in each cardiac cycle during the image acquisition with the magnetic resonance sequence, ultimately the EKG signal can be acquired and evaluated accordingly as a further reference signal during the dead time even in later cardiac cycles (in particular all cardiac cycles) so that an estimation of the interference signals that improves over time results by virtue of the correction signal.

As already explained, the method according to the invention is particularly suitable when a cine-sequence is used as the magnetic resonance sequence. The method according to the invention is not limited to cine-imaging, however, but can be applied to any magnetic resonance sequence that has an at least approximately repetitive gradient pattern that is repeated often enough per cardiac cycle in order to enable a success of the learning algorithm evaluating the reference signal. For example, the method according to the invention can also be applied to the saturation module in multislice perfusion imaging, or even to 3D imaging, wherein the progression of the partition-coding gradient is ignored and each partition coding segment is considered as a repetition. The influences of the gradients for different partitions are essentially the same with regard to the interference signals in the EKG signal.

Imaging procedures known as fluid acquisition, in which the phase shift due to moving blood is used to show blood flow in an MR image, is also a field in which the invention can be used particularly advantageously. Extremely strong gradients are present in such examinations, and consequently significant gradient jumps, such that a particularly pronounced problem exists.

In addition to the method, the present invention also encompasses an EKG trigger device for a magnetic resonance measurement, having an EKG measurement device and a control device designed to implement the method according to the invention. All statements with regard to the method according to the invention apply analogously to the EKG trigger device, with which the advantages of the present invention can consequently also be achieved. Such an EKG trigger device can be connected to a magnetic resonance apparatus or be permanently integrated into such an apparatus. A communication connection is provided between the control device of the magnetic resonance device and the control device of the EKG trigger device, via which the repetition time and/or the offset time (cited with regard to the preparation segments) can be conveyed. The trigger signal generated upon detection of the R-spike can then also be transmitted to the control device of the magnetic resonance device.

BRIEF DESCRIPTION OF THE DRAWINGS

FIG. 1 shows the curve of a pure EKG signal, the curve of interference signals generated by gradient jumps, and the curve of a measured EKG signal within a time frame relevant to the present invention.

FIG. 2 is a flowchart of an embodiment of the method according to the invention.

FIG. 3 schematically illustrates an EKG trigger device according to the invention.

DESCRIPTION OF THE PREFERRED EMBODIMENTS

FIG. 1 shows in detail the problem forming the basis of the invention, and the requirements for its solution via the method according to FIG. 2. In the upper part of FIG. 1, an undistorted EKG signal 1 is schematically depicted over time. The different spikes occurring in the pure EKG signal 1 are known in principle, wherein the most prominent spike (and consequently the spike used for triggering) is the R-spike 2. The R-spike 2 in an actual acquired EKG signal 3 should be detected via a detection algorithm. Whenever the R-spike 2 is detected, a trigger signal is generated, which can be stored and evaluated with acquired magnetic resonance data and/or can equally be used to control the image acquisition operation, for example in order to switch from a "dry run" of the magnetic resonance sequence into an actual acquisition mode in which echoes (MR signals) are acquired. All of this is known in principle to those skilled in the field of MR imaging.

The detection of the R-spike 2 in the actual EKG signal 3 thus should take place parallel to a magnetic resonance measurement, with a magnetic resonance sequence being used (here a cine-magnetic resonance sequence) that includes temporal variations of the gradients (in particular gradient ramps) when gradients are switched (activated). Such temporal variations are designated as gradient jumps in the following. In addition to the pure EKG signal 1, these gradient jumps generate existing interference signals 4 that are shown in the middle graph in FIG. 1. In many magnetic resonance sequences—in particular in flow measurements or the like—the interference signals are extremely strong and localized, such that they can inadvertently be detected as an R-spike 2 by the detection algorithm, or the interference signals can conceal an R-spike 2.

The actual acquired EKG signal 3 shown in the bottom graph in FIG. 1 thus results from an addition of the pure EKG signal 3 and the interference signals 4. For simplicity, additional interference signals (for example interference signals due to the magneto-hydrodynamic effect) are not shown, and are not considered in detail herein because such signals most often have a smaller amplitude and no periodicity.

The inventive method enables a robust detection of the R-spike 2, despite the presence of the interference in signals 4. This is based on a few assumptions that are also shown in FIG. 1. From the pure EKG signal 1, it is apparent that—given an essentially regular heartbeat—the interval between two R-spikes 2 (thus the duration 5 of the cardiac cycle) is quite long. A dead time 6 thus can be derived in which no occurrence of an R-spike 2 is to be expected, for example as two thirds of the duration 5 of the cardiac cycle, or even somewhat more. The duration 5 (in particular 90% of the duration 5) represents the maximum. The duration of the cardiac cycle, moreover, can be derived from the heart rate that is measured anyway.

The cine-sequence used in the exemplary embodiment presented herein makes use of gradients that are repetitively activated, meaning that the gradient jumps respectively repeat after a defined time interval 7 (namely the repetition time TR). This is also clearly apparent in the curve of the interference signals 4, wherein only a few individual interference signals are shown there in order to simplify the presentation, and naturally more complex complete curves can exist. The time interval 7 (the repetition time) is markedly shorter than the duration 5 of the cardiac cycle (shorter by approximately a factor of 9 for exemplary purposes), but naturally magnetic resonance sequences are also known in which the repetition time corresponds to only a tenth or less of the duration of the cardiac cycle.

Likewise, the repeating, periodic occurrence of the interference signals 4 is apparent in the curve of the actual EKG signal 3 because the other spikes of the pure EKG signal 1 and possible magneto-hydrodynamic effects have markedly smaller amplitudes.

The invention is based on the insight to use the dead time 6 after an R-spike 2 in order to learn the curve of the interference signals 4 via a learning algorithm (neural network), and to derive a correction signal that—when it is applied synchronously—largely removes the interference signals 4 from the actual EKG signal 3 if it is subtracted from this.

A curve resulting from the method according to the invention is explained in detail using the illustration in FIG. 2. In Step 8, the detection of the R-spike 2 initially takes place via a detection algorithm before the start of the magnetic resonance measurement, which takes place at the point in time 9 in FIG. 1. This has two consequences. First, a trigger signal is generated that starts the magnetic resonance measurement (consequently the repetitive magnetic resonance sequence) in Step 10. This also is apparent in FIG. 1 by the occurrence of the interference signals 4 after the point in time 9. However, a dead time also begins after the point in time 9, in which dead time the detection algorithm for the R-spike 2 is not active, because no R-spike 2 is expected, but nevertheless the actual EKG signal 3 is acquired as a reference signal (Step 11). As has already been described, the dead time 6 is selected depending on the current heart rate, but is markedly longer than a minimum necessary dead time. Due to the conditions presented with regard to FIG. 1, the dead time 6 includes multiple time intervals 7.

In Step 12, a correction signal is calculated by evaluation of the reference signal, by the repeated interference signals 4 being detected and extracted. An exemplary embodiment is shown in which the repetition time TR (thus the time interval 7) has already been passed to the learning algorithm before the point in time 9 (consequently well before the start of the magnetic resonance measurement), for example via a communication connection to a control device of the magnetic resonance device with which the magnetic resonance data are acquired. This means that the time interval 7 is already known, which simplifies the evaluation of the reference signal. For a specific evaluation, sub-time windows with the length of the time interval 7—which sub-time windows follow one another immediately—are defined within the dead time 6, and the reference signal measured in these sub-time windows is averaged in order to optimally suppress non-periodic effects such as other portions of the pure EKG signal 1 and other interfering effects (for example interfering effects stemming from the magneto-hydrodynamic effect).

After the conclusion of Step 12, not only is a correction signal known that—when it is subtracted from the actual EKG signal—markedly reduces the effects of the interference signals 4, but also it is known (because the sub-time windows have been defined) how the correction signal can be synchronously subtracted for the actual correction, which is always applied at least outside of the dead time 6 according to Step 13.

It is noted that it is naturally also possible to likewise acquire and to evaluate reference signals in additional dead times 6 (thus in the following cardiac cycles) in order to continuously improve the estimation of the correction signal (and thus the correction).

In this way, additional interference signals 4 hindering the detection of the R-spike 2 are largely eliminated.

The method can also be applied to magnetic resonance sequences with a preparation segment in which the periodic repetition of the gradient jumps is not yet present if the duration of said sequences is known, and portions of the reference signal can accordingly be concluded, or the beginning of the magnetic resonance sequence can be adapted in terms of timing so that the preparation segment in the first cardiac cycle (in which the reference signal is acquired) has already elapsed.

Furthermore, the method can be applied to other magnetic resonance sequences in which a periodic repetition of interference signals by the gradient curve is provided.

FIG. 3 shows a block diagram of an EKG trigger device 14 according to the invention, which includes a conventional EKG measurement device 15 in which a control device 16 designed to implement the inventive method is integrated. Not only the detection algorithm to detect the R-spike 2, but also the learning and correction algorithm, are stored in the control device 16, which allow the control device 16 to implement the method according to the invention.

The control device 16 is connected via a communication connection 17 (for example a bus connection) with a control device 18 of the MR apparatus 19 (which is only generally indicated herein). The EKG trigger device 14 can alternatively be integrated into an MR control device 18 that operates the MR apparatus 19.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method to correct an EKG signal, comprising:

operating a magnetic resonance (MR) data acquisition scanner to execute a data acquisition sequence that comprises gradient jumps that repeatedly, respectively occur at respective fixed time intervals from each other;

while operating said MR data acquisition scanner to execute said sequence, acquiring an EKG signal from a patient in the MR data acquisition scanner, said EKG signal comprising a plurality of cardiac cycles each having an R-spike therein that is to be detected and used to trigger acquisition of MR data in said sequence, each cardiac cycle in said plurality of cardiac cycles having a cycle duration that is at least five times said time interval, said EKG signal also comprising interference signals that results from said gradient jumps;

providing said EKG signal to a computer and, in said computer, immediately after the R-spike in a first cardiac cycle of said plurality of cardiac cycles, making no detection of subsequent R-spikes during a dead time that is shorter than said cycle duration, and defining the EKG signal acquired during said dead time as a reference signal;

in said computer, automatically analyzing said reference signal to extract interference signals therefrom that repeat at said time interval and using the extracted interference signals to generate a correction signal having a correction signal duration equal to said time interval;

in said computer, automatically repeating said correction signal and synchronizing the repeated correction signals with said EKG signal and, with the synchronized repeated correction signals, correcting said EKG signal, at least outside of said dead time, to produce a corrected EKG signal that does not exhibit said interference signals; and from said computer, emitting said corrected EKG signal in electronic form, and using R-spikes detected in said corrected EKG signal to trigger acquisition of MR data by said MR data acquisition scanner in said sequence.

2. A method as claimed in claim 1 comprising generating said corrected EKG signal by subtracting said synchronized, repeated correction signals from said EKG signal.

3. A method as claimed in claim 1 wherein each cardiac cycle of said plurality of cardiac cycles has a cycle duration of at least ten times said time interval.

4. A method as claimed in claim 1 comprising starting acquisition of MR data in said sequence no earlier than in said dead time after said R-spike of said first cardiac cycle.

5. A method as claimed in claim 1 comprising providing said computer with a signal representing a current heart rate, and determining said dead time as a fraction of a cardiac cycle determined from said current heart rate.

6. A method as claimed in claim 5 wherein said fraction is in a range between one-third and two-thirds.

7. A method as claimed in claim 1 comprising determining said time interval before analyzing said EKG signal in said computer.

8. A method as claimed in claim 1 comprising, in said computer, defining a plurality of successive time windows in said reference signal, each time window having a time window duration equal to said time interval, and determining said correction signal as an average of signal portions of said reference signal respectively in said time windows.

9. A method as claimed in claim 1 comprising operating said MR data acquisition unit with a sequence, as said data acquisition sequence, that comprises a preparation segment that precedes an MR data acquisition segment, with said gradient jumps not occurring in said preparation segment, and either not acquiring an EKG signal, or performing no analysis in said processor of said EKG signal, during said preparation segment.

10. A method as claimed in claim 1 comprising operating said MR data acquisition scanner with a sequence, as said MR data acquisition sequence, that comprises a preparation segment that precedes an MR data acquisition segment, and, in said computer, selecting said first cardiac cycle dependent on a duration of said preparation segment.

11. A method as claimed in claim 1 comprising defining an additional reference signal from a portion of said EKG signal following said first of said cardiac cycles and using said additional reference signal in said computer to adapt said correction signal.

12. A method as claimed in claim 11 comprising repeatedly occurring respective additional reference signals in respective additional cardiac cycles that follow said first cardiac cycle of said plurality of cardiac cycles, and adapting said correction signal dependent on said additional reference signals in a learning algorithm executed in said computer.

13. A method as claimed in claim 1 comprising operating said MR data acquisition scanner with a cine-sequence as said data acquisition sequence.

14. An EKG trigger device for use with a magnetic resonance (MR) data acquisition scanner that executes a data acquisition sequence that comprises gradient jumps that repeatedly, respectively occur at respective fixed time intervals from each other, said EKG trigger device comprising:

an EKG signal detector comprising electrodes adapted to acquire an EKG signal from a patient in the MR data acquisition scanner while said MR data acquisition scanner is executing said sequence, said EKG signal comprising a plurality of cardiac cycles each having an R-spike therein that is to be detected and used to trigger acquisition of MR data in said sequence, each cardiac cycle of said plurality of cardiac cycles having a cycle duration that is at least five times said time interval, said EKG signal also comprising interference signals that results from said gradient jumps;

a computer provided with said EKG signal, said computer being configured to make no detection of subsequent R-spikes during a dead time that occurs immediately after the R-spike in a first cardiac cycle of said plurality of cardiac cycles, and that is shorter than said cycle duration, and to define the EKG signal acquired during said dead time as a reference signal;

said computer being configured to automatically analyze said reference signal to extract interference signals therefrom that repeat at said time interval and to use the extracted interference signals to generate a correction signal having a correction signal duration equal to said time interval;

said computer being configured to automatically repeat said correction signal and synchronize the repeated correction signals with said EKG signal and, with the synchronized repeated correction signals, correct said EKG signal, at least outside of said dead time, to produce a corrected EKG signal that does not exhibit said interference signals; and said computer being configured to emit said corrected EKG signal in an electronic form that allows R-spikes to be detected in said corrected EKG signal in order to trigger acquisition of said MR data by said MR Data acquisition scanner in said sequence.

* * * * *